(12) United States Patent
Murakami

(10) Patent No.: US 12,357,281 B2
(45) Date of Patent: Jul. 15, 2025

(54) ULTRASOUND DIAGNOSTIC APPARATUS AND A CONTROL METHOD FOR AN ULTRASOUND DIAGNOSTIC APPARATUS IN WHICH A B-MODE IMAGE AND AN M-MODE IMAGE GENERATED BY AN ULTRASOUND PROBE ARE WIRELESSLY TRANSMITTED TO AN APPARATUS MAIN BODY

(71) Applicant: FUJIFILM Corporation, Tokyo (JP)

(72) Inventor: Hiroshi Murakami, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 88 days.

(21) Appl. No.: 18/463,376

(22) Filed: Sep. 8, 2023

(65) Prior Publication Data
US 2023/0414205 A1 Dec. 28, 2023

Related U.S. Application Data

(63) Continuation of application No. PCT/JP2021/045812, filed on Dec. 13, 2021.

(30) Foreign Application Priority Data

Mar. 22, 2021 (JP) .................................. 2021-046985

(51) Int. Cl.
*A61B 8/00* (2006.01)
(52) U.S. Cl.
CPC .............. *A61B 8/56* (2013.01); *A61B 8/4472* (2013.01); *A61B 8/463* (2013.01); *A61B 8/486* (2013.01); *A61B 8/5207* (2013.01)
(58) Field of Classification Search
CPC .......... A61B 8/4472; A61B 8/486; A61B 8/56
See application file for complete search history.

(56) References Cited

U.S. PATENT DOCUMENTS

| 5,570,691 A | * | 11/1996 | Wright | ................. | G10K 11/346 |
| | | | | | 600/447 |
| 2005/0154299 A1 | * | 7/2005 | Hoctor | ................. | A61B 8/4236 |
| | | | | | 600/437 |

(Continued)

FOREIGN PATENT DOCUMENTS

| JP | 2010-125025 A | 6/2010 |
| JP | 2015-514537 A | 5/2015 |

(Continued)

OTHER PUBLICATIONS

International Search Report issued in PCT/JP2021/045812; mailed Mar. 8, 2022.

(Continued)

*Primary Examiner* — Pascal M Bui Pho
*Assistant Examiner* — Nyrobi Celestine
(74) *Attorney, Agent, or Firm* — Studebaker Brackett PLLC

(57) ABSTRACT

There is provided an ultrasound diagnostic apparatus including an ultrasound probe and an apparatus main body wirelessly connected to the ultrasound probe, the ultrasound probe including a B-mode processing unit and an M-mode processing unit configured to generate a B-mode image and an M-mode image, a wireless communication circuit configured to wirelessly transmit the B-mode image and the M-mode image to the apparatus main body, and a probe control unit configured to control the wireless communication circuit such that, each time a generation of a certain number of scanning lines in the B-mode image, which is less than the number of scanning lines in a single frame of the B-mode image, is completed, wireless transmission of the certain number of scanning lines in the B-mode image and wireless transmission of the M-mode image are alternately performed.

20 Claims, 6 Drawing Sheets

(56) References Cited

U.S. PATENT DOCUMENTS

| | | | |
|---|---|---|---|
| 2011/0224548 A1 | 9/2011 | Otaki | |
| 2015/0087987 A1 | 3/2015 | Ryu et al. | |
| 2015/0164477 A1* | 6/2015 | Ryu .................. | A61B 8/56 |
| | | | 600/443 |
| 2016/0066893 A1* | 3/2016 | Cho .................. | A61B 8/54 |
| | | | 600/459 |
| 2016/0310110 A1* | 10/2016 | Dodd ................ | A61B 8/54 |
| 2018/0168554 A1* | 6/2018 | Song ............. | H04W 52/0261 |
| 2020/0287993 A1* | 9/2020 | Schweizer .......... | H04L 67/125 |
| 2021/0015459 A1* | 1/2021 | Miyachi ............ | A61B 8/461 |

FOREIGN PATENT DOCUMENTS

| | | |
|---|---|---|
| WO | 2010/055879 A1 | 5/2010 |
| WO | 2019/208166 A1 | 10/2019 |

OTHER PUBLICATIONS

Written Opinion of the International Searching Authority issued in PCT/JP2021/045812; mailed Mar. 8, 2022.

* cited by examiner

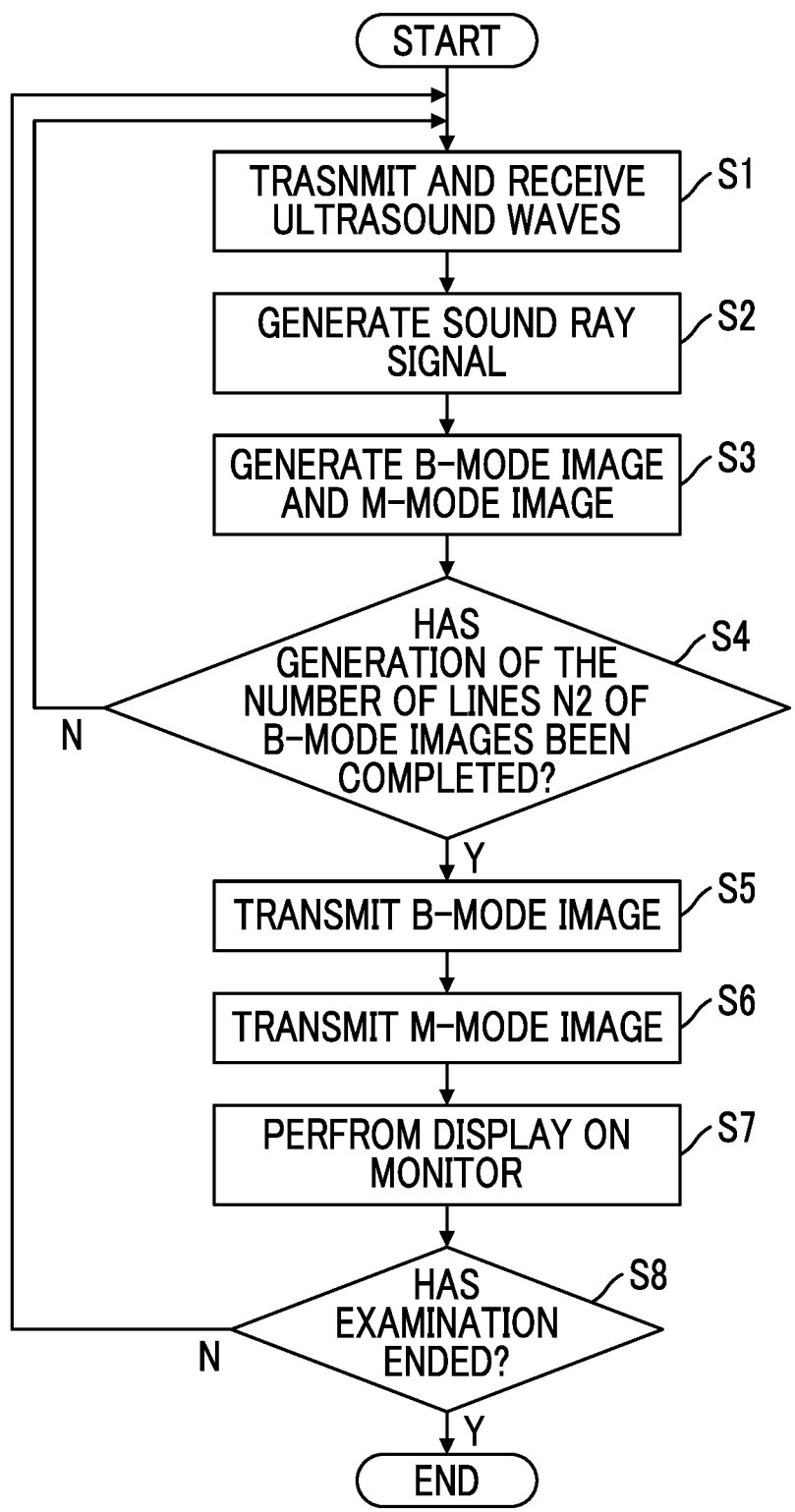

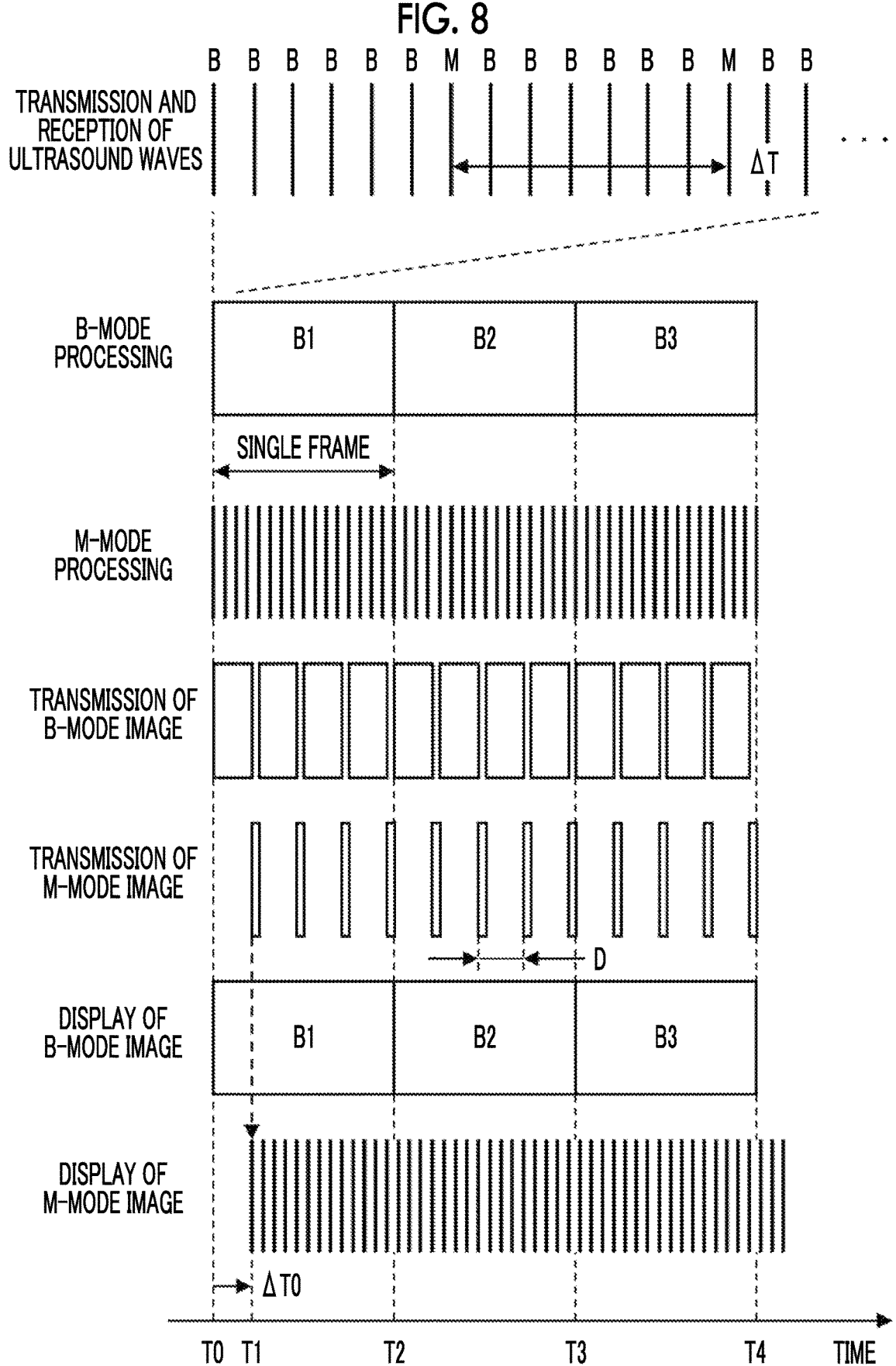

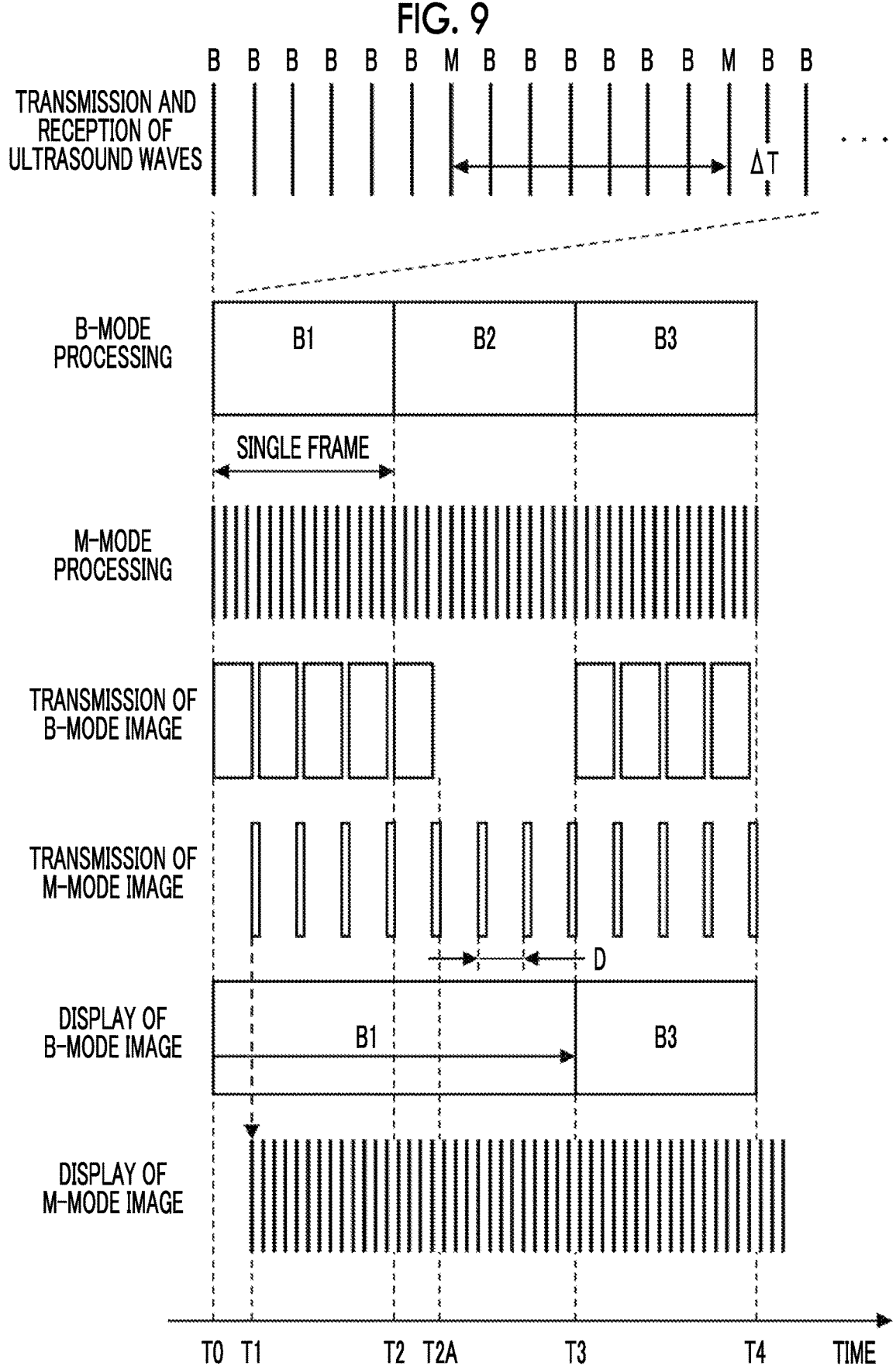

ULTRASOUND DIAGNOSTIC APPARATUS AND A CONTROL METHOD FOR AN ULTRASOUND DIAGNOSTIC APPARATUS IN WHICH A B-MODE IMAGE AND AN M-MODE IMAGE GENERATED BY AN ULTRASOUND PROBE ARE WIRELESSLY TRANSMITTED TO AN APPARATUS MAIN BODY

CROSS-REFERENCE TO RELATED APPLICATIONS

This application is a Continuation of PCT International application No. PCT/JP2021/045812 filed on Dec. 13, 2021, which claims priority under 35 U.S.C. § 119(a) to Japanese Patent application No. 2021-046985 filed on Mar. 22, 2021. The above applications are hereby expressly incorporated by reference, in their entirety, into the present application.

BACKGROUND OF THE INVENTION

1. Field of the Invention

The present invention relates to an ultrasound diagnostic apparatus and a control method for an ultrasound diagnostic apparatus, and particularly, to an ultrasound diagnostic apparatus and a control method for an ultrasound diagnostic apparatus in which a brightness mode (B-mode) image and a motion mode (M-mode) image, which are generated by an ultrasound probe, are wirelessly transmitted to an apparatus main body.

2. Description of the Related Art

Hitherto, in the medical field, an ultrasound diagnostic apparatus using an ultrasound image has been put to practical use. In general, this type of ultrasound diagnostic apparatus comprises an ultrasound probe incorporating a transducer array, and an apparatus main body connected to the ultrasound probe, and an ultrasound beam is transmitted from the transducer array of the ultrasound probe toward a subject under examination, an ultrasound echo from the subject under examination is received by the transducer array, and a reception signal is electrically processed, so that an ultrasound image is generated and displayed on a monitor of the apparatus main body.

As disclosed in JP2015-514537A, recently, an ultrasound diagnostic apparatus has been developed to improve operability and mobility of an ultrasound probe by establishing a wireless connection between the ultrasound probe and an apparatus main body through wireless communication. In the apparatus disclosed in JP2015-514537A, an ultrasound image is generated within the ultrasound probe, is subjected to compression processing, and is then wirelessly transmitted to the apparatus main body.

In addition, JP2010-125025A discloses an ultrasound diagnostic apparatus that generates and displays both a B-mode image and an M-mode image as ultrasound images. The M-mode image represents a temporal change in the brightness on a single scanning line in the B-mode image and is a useful image for observing a site with motion in time series.

SUMMARY OF THE INVENTION

In a case where an ultrasound probe wirelessly connected to an apparatus main body as in the ultrasound diagnostic apparatus disclosed in JP2015-514537A generates and wirelessly transmits both a B-mode image and an M-mode image as in JP2010-125025A to the apparatus main body, it is desired to compress each of the B-mode image and the M-mode image and then to wirelessly transmit the images to the apparatus main body in order to ensure stability in image transmission. In addition, in this case, it is preferable to prioritize the compression of two-dimensional images from the viewpoint of compression efficiency.

In that respect, the B-mode image, which is a two-dimensional image, is compressed and wirelessly transmitted from the ultrasound probe to the apparatus main body on a frame-by-frame basis, and the M-mode image is compressed and then wirelessly transmitted from the ultrasound probe to the apparatus main body at any time outside a transmission period of the B-mode image.

However, the M-mode image cannot be transmitted during the period in which the B-mode image is transmitted on a frame-by-frame basis. Therefore, there is a problem where a display frame rate of the M-mode image in the apparatus main body partially fluctuates, which may make it difficult to smoothly update a screen display.

As a result, there is a risk that it becomes difficult to perform intuitive diagnosis by observing the M-mode image displayed on the monitor of the apparatus main body, which may lead to a decrease in convenience.

The present invention has been made in order to solve such a conventional problem, and an object of the present invention is to provide an ultrasound diagnostic apparatus and a control method for an ultrasound diagnostic apparatus capable of smoothly displaying an M-mode image in an apparatus main body while wirelessly transmitting a B-mode image and the M-mode image from an ultrasound probe to the apparatus main body.

In order to achieve the above-described object, according to the present invention, there is provided an ultrasound diagnostic apparatus comprising:

an ultrasound probe including a transducer array; and
an apparatus main body wirelessly connected to the ultrasound probe and including a monitor,
in which the ultrasound probe includes
a B-mode processing unit and an M-mode processing unit configured to generate a B-mode image and an M-mode image, respectively, based on reception signals acquired by performing ultrasound scanning using the transducer array,
a wireless communication circuit configured to wirelessly transmit the B-mode image and the M-mode image to the apparatus main body, and
a probe control unit configured to control the wireless communication circuit such that, each time generation of a certain number of lines of B-mode images, which is less than the number of scanning lines in a single frame of the B-mode image, is completed, wireless transmission of the certain number of lines of B-mode images generated by the B-mode processing unit and wireless transmission of the M-mode image generated by the M-mode processing unit are alternately performed, and
the B-mode image and the M-mode image wirelessly transmitted from the ultrasound probe to the apparatus main body are displayed on the monitor.

It is preferable that the ultrasound probe includes a B-mode image compression processing unit configured to compress the B-mode image and an M-mode image compression processing unit configured to compress the M-mode image, and that the certain number of lines is a unit number of compression lines in the B-mode image compression processing unit.

It is preferable that the probe control unit is configured to control the wireless communication circuit such that the wireless communication circuit preferentially transmits the M-mode image and discards an untransmitted B-mode image in a case where a wireless transmission rate in the wireless communication circuit falls to or below a predetermined rate threshold value.

In addition, the wireless communication circuit may also be configured to make a unit number of lines for the wireless transmission of the M-mode image variable according to a wireless transmission rate.

It is preferable that the probe control unit is configured to control the wireless communication circuit to discard an untransmitted M-mode image in a case where a delay amount of the wireless transmission of the M-mode image by the wireless communication circuit exceeds a predetermined delay threshold value.

Further, the apparatus main body may be configured to, in a case where there is a loss in the M-mode image wirelessly transmitted from the ultrasound probe, display the M-mode image on the monitor with the loss blanked out.

According to the present invention, there is provided a control method for an ultrasound diagnostic apparatus in which an apparatus main body is wirelessly connected to an ultrasound probe including a transducer array, the control method comprising:
  generating a B-mode image and an M-mode image through the ultrasound probe based on reception signals acquired by performing ultrasound scanning using the transducer array;
  alternately performing, each time generation of a certain number of lines of B-mode images, which is less than the number of scanning lines in a single frame of the B-mode image, is completed, wireless transmission of the generated certain number of lines of B-mode images from the ultrasound probe to the apparatus main body and wireless transmission of the generated M-mode image from the ultrasound probe to the apparatus main body; and
  displaying the B-mode image and the M-mode image wirelessly transmitted from the ultrasound probe to the apparatus main body on a monitor of the apparatus main body.

It is preferable that the B-mode image and the M-mode image are each compressed and then wirelessly transmitted to the apparatus main body, and that the certain number of lines is a unit number of compression lines for the B-mode image.

It is preferable that, in a case where a wireless transmission rate from the transducer array to the apparatus main body falls to or below a predetermined rate threshold value, the M-mode image is preferentially transmitted, and an untransmitted B-mode image is discarded.

In addition, a unit number of lines for the wireless transmission of the M-mode image may also be made variable according to a wireless transmission rate from the transducer array to the apparatus main body.

It is preferable that, in a case where a delay amount of the wireless transmission of the M-mode image exceeds a predetermined delay threshold value, an untransmitted M-mode image is discarded.

Further, in a case where there is a loss in the M-mode image wirelessly transmitted from the ultrasound probe, the M-mode image may be displayed on the monitor with the loss blanked out.

According to the present invention, the ultrasound probe includes the probe control unit configured to control the wireless communication circuit such that, each time generation of a certain number of lines of B-mode images, which is less than the number of scanning lines in a single frame of the B-mode image, is completed, wireless transmission of the certain number of lines of B-mode images generated by the B-mode processing unit and wireless transmission of the M-mode image generated by the M-mode processing unit are alternately performed. Therefore, it is possible to smoothly display the M-mode image in the apparatus main body while wirelessly transmitting the B-mode image and the M-mode image from the ultrasound probe to the apparatus main body.

BRIEF DESCRIPTION OF THE DRAWINGS

FIG. 7 is a flowchart showing an operation of the ultrasound diagnostic apparatus according to the embodiment.

FIG. 8 is a timing chart showing a series of processes from transmission and reception of ultrasound waves to display of the B-mode image and the M-mode image in the embodiment.

FIG. 9 is a timing chart showing a series of processes from transmission and reception of ultrasound waves to display of the B-mode image and the M-mode image in an ultrasound diagnostic apparatus of a modification example.

DESCRIPTION OF THE PREFERRED EMBODIMENTS

Hereinafter, an embodiment of the present invention will be described with reference to the accompanying drawings.

The description of configuration requirements to be described below is made based on a representative embodiment of the present invention, but the present invention is not limited to such an embodiment.

In the present specification, a numerical range represented by "to" means a range including numerical values described before and after "to" as a lower limit value and an upper limit value, respectively.

In the present specification, "same" and "identical" include an error range generally allowed in the technical field.

Figure 1:
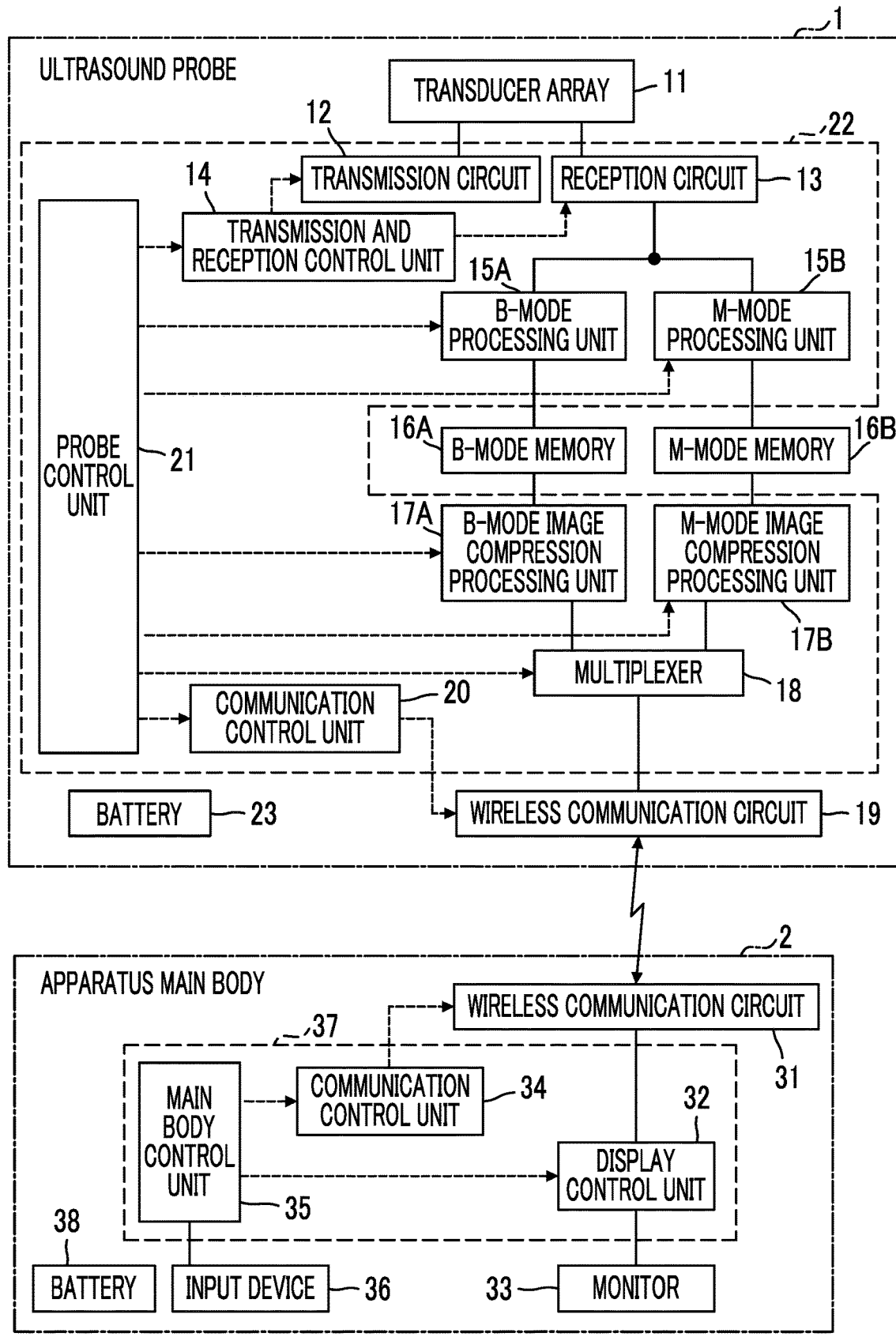
FIG. 1 is a block diagram showing a configuration of an ultrasound diagnostic apparatus according to an embodiment of the present invention.

FIG. 1 shows a configuration of an ultrasound diagnostic apparatus according to the embodiment of the present invention. The ultrasound diagnostic apparatus is an ultrasound diagnostic apparatus that includes an ultrasound probe 1 and an apparatus main body 2 wirelessly connected to the ultrasound probe 1 and that generates and displays a brightness mode (B-mode) image and a motion mode (M-mode) image.

As shown in FIG. 1, the ultrasound probe 1 includes a transducer array 11, and a transmission circuit 12 and a reception circuit 13 are connected to the transducer array 11. A transmission and reception control unit 14 is connected to the transmission circuit 12 and the reception circuit 13, and a B-mode processing unit 15A and an M-mode processing unit 15B are connected in parallel to the reception circuit 13. A B-mode memory 16A and a B-mode image compression processing unit 17A are sequentially connected to the B-mode processing unit 15A, and an M-mode memory 16B and an M-mode image compression processing unit 17B are sequentially connected to the M-mode processing unit 15B.

In addition, a multiplexer 18 is connected to the B-mode image compression processing unit 17A and the M-mode image compression processing unit 17B, a wireless communication circuit 19 is connected to the multiplexer 18, and a communication control unit 20 is connected to the wireless communication circuit 19.

A probe control unit 21 is connected to the transmission and reception control unit 14, the B-mode processing unit 15A, the M-mode processing unit 15B, the B-mode image compression processing unit 17A, the M-mode image compression processing unit 17B, the multiplexer 18, and the communication control unit 20.

A probe side processor 22 is composed of the transmission circuit 12, the reception circuit 13, the transmission and reception control unit 14, the B-mode processing unit 15A, the M-mode processing unit 15B, the B-mode image compression processing unit 17A, the M-mode image compression processing unit 17B, the multiplexer 18, the communication control unit 20, and the probe control unit 21.

Further, the ultrasound probe 1 incorporates a battery 23.

Meanwhile, the apparatus main body 2 includes a wireless communication circuit 31, and a display control unit 32 and a monitor 33 are sequentially connected to the wireless communication circuit 31. In addition, a communication control unit 34 is connected to the wireless communication circuit 31, and a main body control unit 35 is connected to the display control unit 32 and the communication control unit 34. Further, an input device 36 is connected to the main body control unit 35.

A main body side processor 37 is composed of the display control unit 32, the communication control unit 34, and the main body control unit 35.

Further, the apparatus main body 2 incorporates a battery 38.

The transducer array 11 of the ultrasound probe 1 includes a plurality of ultrasound transducers one-dimensionally or two-dimensionally arranged. Each of these transducers transmits an ultrasound wave in accordance with a drive signal supplied from the transmission circuit 12 and outputs an analog reception signal by receiving a reflected wave from the subject under examination. For example, each transducer is composed of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like, and electrodes formed at both ends of the piezoelectric body.

The transmission circuit 12 includes, for example, a plurality of pulse generators and supplies respective drive signals to the plurality of transducers by adjusting delay amounts such that ultrasound waves transmitted from the plurality of transducers of the transducer array 11 form an ultrasound beam, based on a transmission delay pattern selected according to a control signal from the transmission and reception control unit 14. In this way, in a case where a pulsed or continuous-wave voltage is applied to the electrodes of the transducer of the transducer array 11, the piezoelectric body expands and contracts, and a pulsed or continuous-wave ultrasound wave is generated from each of the transducers, so that the ultrasound beam is formed from a combined wave of these ultrasound waves.

The transmitted ultrasound beam is reflected in, for example, a target such as a site of the subject under examination, and an ultrasound echo propagates toward the transducer array 11. The ultrasound echo propagating toward the transducer array 11 in this way is received by each of the transducers constituting the transducer array 11. At this time, each of the transducers constituting the transducer array 11 expands and contracts by receiving the propagating ultrasound echo, and generates a reception signal (electrical signal), thereby outputting these reception signals to the reception circuit 13.

Figure 2:
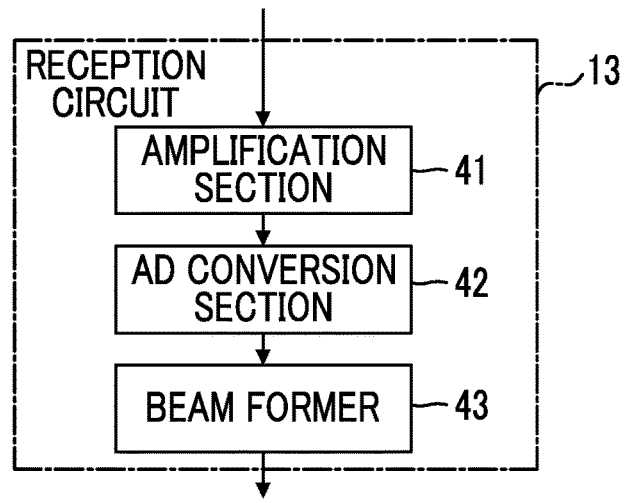
FIG. 2 is a block diagram showing an internal configuration of a reception circuit in the embodiment.

The reception circuit 13 processes the signals output from the transducer array 11 in accordance with a control signal from the transmission and reception control unit 14 to generate a sound ray signal. As shown in FIG. 2, the reception circuit 13 has a configuration in which an amplification section 41, an analog-to-digital (AD) conversion section 42, and a beam former 43 are connected in series.

The amplification section 41 amplifies the reception signal, which is an analog signal input from each of the transducers constituting the transducer array 11, and transmits the amplified reception signal to the AD conversion section 42.

The AD conversion section 42 converts the analog reception signal transmitted from the amplification section 41 into a digital signal to acquire reception data and sends out the reception data to the beam former 43.

The beam former 43 performs so-called reception focus processing of performing addition (phase addition) by applying a delay to each reception data following a set sound velocity based on a reception delay pattern selected according to a control signal from the transmission and reception control unit 14. By performing this reception focus processing, a sound ray signal in which the focus of the ultrasound echo is narrowed down is generated.

The transmission and reception control unit 14 controls the transmission circuit 12 and the reception circuit 13 to transmit the ultrasound beam and receive the ultrasound echo based on an examination mode and a scanning method as instructed by the probe control unit 21. Here, the examination modes include available examination modes in the ultrasound diagnostic apparatus, including at least a B-mode and an M-mode, and the scanning method indicates, for example, any one of an electronic sector scanning method, an electronic linear scanning method, an electronic convex scanning method, or the like.

Figure 3:
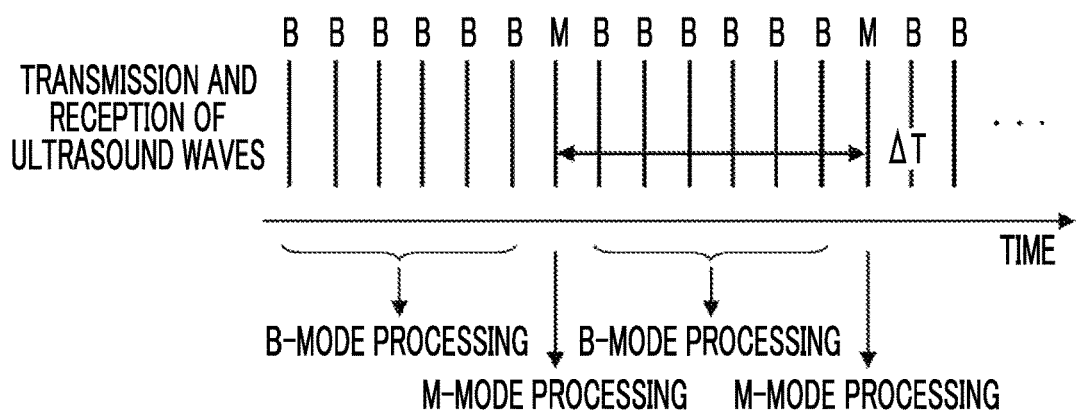
FIG. 3 is a timing chart showing a state of transmission and reception of ultrasound waves in a case where an examination in a B-mode and an examination in an M-mode are executed at the same time.

The examination in the B-mode and the examination in the M-mode may be executed at the same time. In this case, as shown in FIG. 3, the transmission and reception control unit 14 controls the transmission circuit 12 and the reception circuit 13 such that a series of transmissions and receptions of ultrasound waves for performing scanning from one end to the other end of a sub-scanning direction (an azimuth direction orthogonal to a depth direction) in an imaging region of the B-mode image and transmission and reception of ultrasound waves to be repeated at a predetermined time interval ΔT along a single scanning line SL designated in order to capture the M-mode image are performed in a time-division manner.

That is, by repeating sequentially performing transmissions and receptions of ultrasound waves along the respective corresponding scanning lines toward the sub-scanning direction, and then performing one transmission and reception of ultrasound waves along the single scanning line SL for capturing the M-mode image, sequentially performing transmissions and receptions of ultrasound waves along the respective corresponding scanning lines again toward the sub-scanning direction, and further performing one transmission and reception of ultrasound waves along the single scanning line SL for capturing the M-mode image, sound ray signals corresponding to a single frame of the B-mode image and sound ray signals corresponding to the M-mode image are acquired by the reception circuit 13.

Similarly, sound ray signals corresponding to a plurality of consecutive frames of B-mode images and sound ray signals corresponding to the M-mode image are acquired. The sound ray signal corresponding to the B-mode image is transmitted from the reception circuit 13 to the B-mode processing unit 15A, and the sound ray signal corresponding to the M-mode image is transmitted from the reception circuit 13 to the M-mode processing unit 15B.

Figure 4:
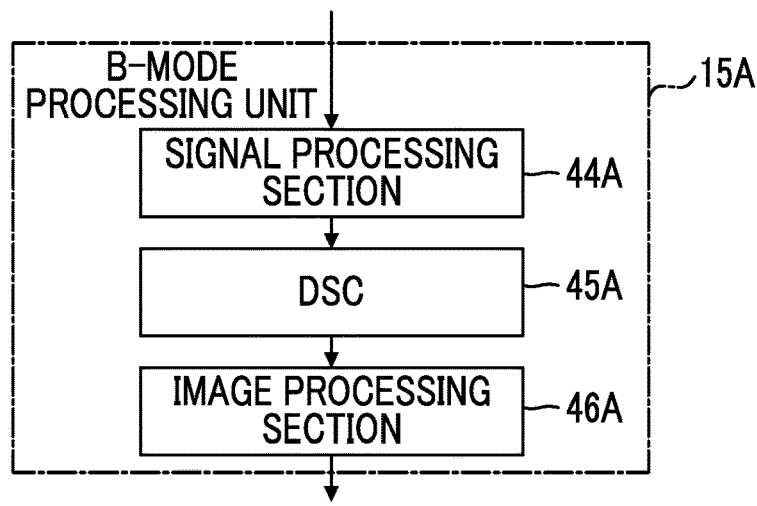
FIG. 4 is a block diagram showing an internal configuration of a B-mode processing unit in the embodiment.

The B-mode processing unit 15A generates a so-called B-mode image based on the sound ray signal corresponding to the B-mode image generated by the reception circuit 13. As shown in FIG. 4, the B-mode processing unit 15A has a configuration in which a signal processing section 44A, a digital scan converter (DSC) 45A, and an image processing section 46A are sequentially connected in series.

The signal processing section 44A generates a B-mode image signal, which is tomographic image information regarding the internal tissues of the subject under examination, by performing envelope detection processing after correcting the attenuation caused by a distance according to the depth of the position where ultrasound waves are reflected, with respect to the sound ray signal corresponding to the B-mode image generated by the reception circuit 13.

The DSC 45A converts (raster-converts) the B-mode image signal generated by the signal processing section 44A into an image signal according to a normal television signal scanning method.

The image processing section 46A performs various types of necessary image processing, such as gradation processing, on the B-mode image signal input from the DSC 45A and then sends out the B-mode image signal (hereinafter, referred to as a B-mode image), which has been subjected to image processing, to the B-mode memory 16A.

Figure 5:
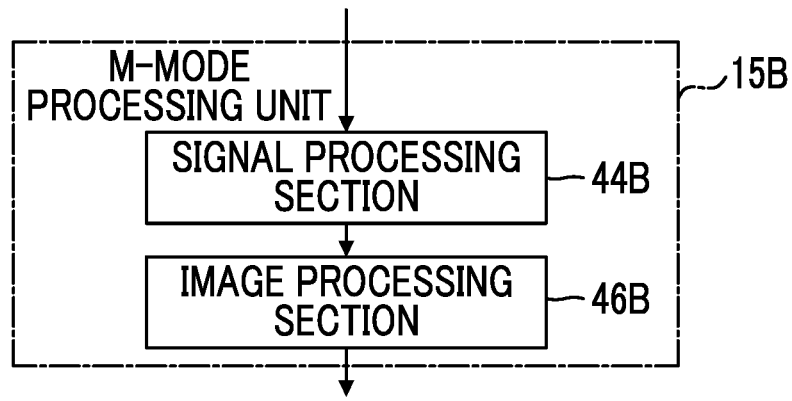
FIG. 5 is a block diagram showing an internal configuration of an M-mode processing unit in the embodiment.

The M-mode processing unit 15B generates a so-called M-mode image based on the sound ray signal corresponding to the M-mode image generated by the reception circuit 13. As shown in FIG. 5, the M-mode processing unit 15B has a configuration in which a signal processing section 44B and an image processing section 46B are connected in series.

The signal processing section 44B generates an M-mode image signal by performing envelope detection processing after correcting the attenuation caused by a distance according to the depth of the position where ultrasound waves are reflected, with respect to the sound ray signal corresponding to the M-mode image generated by the reception circuit 13. In the M-mode image, the horizontal axis represents the time axis, and the vertical axis represents the brightness on the single scan line SL, and temporal changes in the brightness distribution on the single scan line SL are imaged.

The image processing section 46B performs various types of necessary image processing, such as gradation processing, on the M-mode image signal input from the signal processing section 44B and then sends out the M-mode image signal (hereinafter, referred to as an M-mode image), which has been subjected to image processing, to the M-mode memory 16B.

The B-mode memory 16A is a buffer memory that temporarily stores the B-mode image generated by the B-mode processing unit 15A.

Similarly, the M-mode memory 16B is a buffer memory that temporarily stores the M-mode image generated by the M-mode processing unit 15B.

The B-mode image compression processing unit 17A compresses the B-mode image stored in the B-mode memory 16A into a format such as a so-called joint photographic experts group (JPEG). Specifically, in the B-mode image compression processing unit 17A, for example, a unit number of compression lines, such as 8 lines, are set, and compression of the B-mode images is performed for each unit number of compression lines.

Similarly, the M-mode image compression processing unit 17B performs one-dimensional compression, such as differential compression, on the M-mode image stored in the M-mode memory 16B.

Under the control of the probe control unit 21, the multiplexer 18 selectively sends out the B-mode image compressed by the B-mode image compression processing unit 17A and the M-mode image compressed by the M-mode image compression processing unit 17B to the wireless communication circuit 19.

The wireless communication circuit 19 sequentially wirelessly transmits the B-mode image and the M-mode image selected by the multiplexer 18 to the apparatus main body 2.

More specifically, the wireless communication circuit 19 includes an antenna for transmitting and receiving radio waves, and modulates a carrier based on the B-mode image and the M-mode image to generate a transmission signal and supplies the transmission signal to the antenna to transmit the radio waves from the antenna, thereby wirelessly transmitting the B-mode image and the M-mode image to the apparatus main body 2. As a carrier modulation method, amplitude shift keying (ASK), phase shift keying (PSK), quadrature phase shift keying (QPSK), 16 quadrature amplitude modulation (16QAM), and the like are used.

The communication control unit 20 controls the wireless communication circuit 19 such that the B-mode image and the M-mode image are transmitted at a transmission radio wave intensity set by the probe control unit 21.

The probe control unit 21 controls each unit of the ultrasound probe 1 based on a program or the like stored in advance.

In addition, the probe control unit 21 controls the multiplexer 18 and the wireless communication circuit 19 such that, each time the generation of a certain number of lines N2 of B-mode images, which is less than the number of scanning lines N1 in a single frame of the B-mode image, is completed by the B-mode processing unit 15A, the wireless transmission of the certain number of lines N2 of B-mode images to the apparatus main body 2 and the wireless transmission of the M-mode image generated by the M-mode processing unit 15B to the apparatus main body 2 are alternately performed in a case where the examination in the B-mode and the examination in the M-mode are executed at the same time.

Here, the certain number of lines N2, which is less than the number of scanning lines N1 in a single frame of the B-mode image, can be set, for example, as the unit number of compression lines in the B-mode image compression processing unit 17A. That is, each time the B-mode image compression processing unit 17A completes the compression processing of the unit number of compression lines, strip-shaped B-mode images corresponding to the unit number of compression lines are sent out from the B-mode image compression processing unit 17A to the wireless communication circuit 19 via the multiplexer 18 and are wirelessly transmitted to the apparatus main body 2, and subsequently, the M-mode image corresponding to the unit number of compression lines and subjected to the compression processing by the M-mode image compression processing unit 17B is sent out from the M-mode image compression processing unit 17B to the wireless communication circuit 19 via the multiplexer 18 and is wirelessly transmitted to the apparatus main body 2.

Further, the battery 23 is incorporated into the ultrasound probe 1 and supplies power to each circuit in the ultrasound probe 1.

The probe side processor 22 including the transmission circuit 12, the reception circuit 13, the transmission and reception control unit 14, the B-mode processing unit 15A, the M-mode processing unit 15B, The B-mode image compression processing unit 17A, the M-mode image compression processing unit 17B, the multiplexer 18, the communication control unit 20, and the probe control unit 21 of the ultrasound probe 1 is composed of a central processing unit (CPU) that executes various programs and a control program for causing the CPU to perform various types of processing, but the probe side processor 22 may be composed of a field programmable gate array (FPGA), a digital signal processor (DSP), an application specific integrated circuit (ASIC), a graphics processing unit (GPU), or other integrated circuits (ICs), or may be composed of a combination thereof.

In addition, the transmission circuit 12, the reception circuit 13, the transmission and reception control unit 14, the B-mode processing unit 15A, the M-mode processing unit 15B, The B-mode image compression processing unit 17A, the M-mode image compression processing unit 17B, the multiplexer 18, the communication control unit 20, and the probe control unit 21 of the probe side processor 22 can also be configured by being partially or wholly integrated into one CPU or the like.

The wireless communication circuit 31 of the apparatus main body 2 receives the B-mode image and the M-mode image wirelessly transmitted from the wireless communication circuit 19 of the ultrasound probe 1.

More specifically, the wireless communication circuit 31 includes an antenna for transmitting and receiving radio waves, and receives a transmission signal transmitted by the wireless communication circuit 19 of the ultrasound probe 1 via the antenna and demodulates the received transmission signal to send out the B-mode image and the M-mode image to the display control unit 32.

Figure 6:
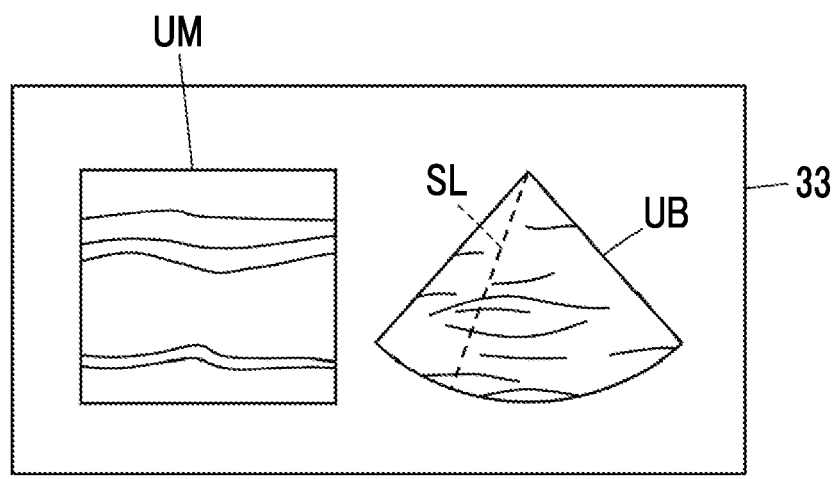
FIG. 6 is a diagram showing a B-mode image and an M-mode image displayed on a monitor.

The display control unit 32 causes the monitor 33 to display the B-mode image and the M-mode image received via the wireless communication circuit 31 as display images. Specifically, as shown in FIG. 6, the display control unit 32 displays a B-mode image UB and an M-mode image UM side by side on the screen of the monitor 33.

The monitor 33 is controlled by the display control unit 32 to display the B-mode image UB and the M-mode image UM as the display images, and examples thereof include a display device, such as a liquid crystal display (LCD) and an organic electroluminescence display (organic EL display).

The communication control unit 34 controls the wireless communication circuit 31 such that the transmission signal transmitted from the wireless communication circuit 19 of the ultrasound probe 1 is received.

The main body control unit 35 controls each unit of the apparatus main body 2 based on a program stored in advance in a storage unit (not shown) or the like and an input operation performed by an operator via the input device 36.

The input device 36 is used for the operator to perform an input operation, and can be configured by a keyboard, a mouse, a trackball, a touch pad, a touch panel, or the like. A configuration can also be employed in which a touch sensor is combined with the monitor 33 and the touch sensor is used as the input device 36.

The battery 38 supplies power to each circuit in the apparatus main body 2. The apparatus main body 2 can also be configured to supply power to each circuit in the apparatus main body 2 by drawing power from a commercial power source without incorporating the battery 38.

The main body side processor 37 including the display control unit 32, the communication control unit 34, and the main body control unit 35 of the apparatus main body 2 is composed of a CPU and a control program for causing the CPU to perform various types of processing, but the main body side processor 37 may be composed of FPGA, DSP, ASIC, GPU, or other ICs, or may be composed of a combination thereof.

In addition, the display control unit 32, the communication control unit 34, and the main body control unit 35 of the main body side processor 37 can also be configured by being partially or wholly integrated into one CPU or the like.

Next, the operation of the ultrasound diagnostic apparatus in a case where the examination in the B-mode and the examination in the M-mode are executed at the same time will be described with reference to the flowchart of FIG. 7.

First, in step S1, transmission and reception of ultrasound waves are performed by the ultrasound probe 1. In this case, in the ultrasound probe 1, ultrasound beams are transmitted into the subject under examination from the plurality of transducers of the transducer array 11 in accordance with a drive signal from the transmission circuit 12 under the control of the transmission and reception control unit 14. The ultrasound echo by the subject under examination is received by the plurality of transducers of the transducer array 11, and the reception signal, which is an analog signal, is output from the plurality of transducers to the reception circuit 13.

As shown in FIG. 3, a series of transmissions and receptions of ultrasound waves for performing scanning from one end to the other end of the sub-scanning direction and transmission and reception of ultrasound waves to be repeated at the predetermined time interval $\Delta T$ along the single scanning line SL designated in order to capture the M-mode image are performed in a time-division manner.

In subsequent step S2, the reception signal is amplified by the amplification section 41 of the reception circuit 13, subjected to AD conversion by the AD conversion section 42, and then subjected to reception focus processing by the beam former 43, whereby the sound ray signals are generated, and the sound ray signal corresponding to the B-mode image is sent out from the reception circuit 13 to the B-mode processing unit 15A, and the sound ray signal corresponding to the M-mode image is sent out from the reception circuit 13 to the M-mode processing unit 15B.

Further, in step S3, the sound ray signal corresponding to the B-mode image is input to the B-mode processing unit 15A, and the B-mode image is generated by the B-mode processing unit 15A, and the sound ray signal corresponding to the M-mode image is input to the M-mode processing unit 15B, and the M-mode image is generated by the M-mode processing unit 15B in parallel with the generation of the B-mode image.

At this time, the B-mode image signal is generated by correcting the attenuation caused by the distance according to the depth of the position where ultrasound waves are reflected and performing the envelope detection processing through the signal processing section 44A of the B-mode processing unit 15A, is converted into the image signal according to the normal television signal scanning method by the DSC 45A, and is further subjected to various types of necessary image processing, such as gradation processing, through the image processing section 46A, so that the B-mode image is generated and stored in the B-mode memory 16A.

Similarly, the M-mode image signal is generated by correcting the attenuation caused by the distance according to the depth of the position where ultrasound waves are reflected and performing the envelope detection processing through the signal processing section 44B of the M-mode processing unit 15B, and is further subjected to various types of necessary image processing, such as gradation processing, through the image processing section 46B, so that M-mode image is generated and stored in the M-mode memory 16B.

The B-mode images stored in the B-mode memory 16A are sequentially compressed by the B-mode image compression processing unit 17A. Specifically, the B-mode image is compressed for each unit number of compression lines set in the B-mode image compression processing unit 17A.

Similarly, the M-mode images stored in the M-mode memory 16B are sequentially compressed by the M-mode image compression processing unit 17B. Specifically, the M-mode image is compressed for each unit number of compression lines set in the M-mode image compression processing unit 17B.

In a case where the B-mode image and the M-mode image are each generated and the compression processing is performed in this manner, in step S4, it is determined whether or not the generation of the certain number of lines N2 of B-mode images, which is less than the number of scanning lines N1 in a single frame of the B-mode image, has been completed. For example, it is determined whether or not the compression of the unit number of compression lines of B-mode images, which is set as the number of lines N2, has been completed by the B-mode image compression processing unit 17A.

Then, in a case where it is determined that the compression of the unit number of compression lines of B-mode images has been completed, it is determined that the generation of the number of lines N2 of B-mode images has been completed. The process proceeds to step S5, and the B-mode image compressed by the B-mode image compression processing unit 17A is selected by the multiplexer 18 and wirelessly transmitted from the wireless communication circuit 19 to the apparatus main body 2.

After the wireless transmission of the B-mode image in step S5 is completed, in subsequent step S6, the M-mode image compressed by the M-mode image compression processing unit 17B is selected by the multiplexer 18 and wirelessly transmitted from the wireless communication circuit 19 to the apparatus main body 2.

The B-mode image and the M-mode image sequentially wirelessly transmitted to the apparatus main body 2 are received by the wireless communication circuit 31 of the apparatus main body 2 and transmitted to the monitor 33 via the display control unit 32. As a result, as shown in FIG. 6, in step S7, the B-mode image UB and the M-mode image UM are displayed on the screen of the monitor 33.

After that, in step S8, it is determined whether or not a series of examinations has ended, and in a case where it is determined that the examination has not ended, the process returns to step S1, and steps S1 to S7 are repeated.

As a result of the determination in step S4, in a case where it is determined that the compression of the unit number of compression lines of B-mode images, which is set as the number of lines N2, has not been completed by the B-mode image compression processing unit 17A, the process returns to step S1, and steps S1 to S3 are repeated until it is determined that the compression of the unit number of compression lines of B-mode images has been completed.

Here, in the embodiment, a series of processes from transmission and reception of ultrasound waves by the ultrasound probe 1 to display of the B-mode image UB and the M-mode image UM on the monitor 33 of the apparatus main body 2 is shown in the timing chart of FIG. 8.

In a case where the transmission and reception of ultrasound waves are started at time T0, a series of transmissions and receptions of ultrasound waves for performing scanning from one end to the other end of the sub-scanning direction and transmission and reception of ultrasound waves to be repeated at the predetermined time interval $\Delta T$ along the single scanning line SL designated in order to capture the M-mode image are performed in a time-division manner.

The sound ray signal corresponding to the B-mode image is processed and the B-mode image is generated by the B-mode processing unit 15A, and the sound ray signal corresponding to the M-mode image is processed and the M-mode image is generated by the M-mode processing unit 15B in parallel with the generation of the B-mode image.

Then, in a case where the compression of the number of lines N2 of B-mode images, which is the unit number of compression lines, is completed by the B-mode image compression processing unit 17A, the number of lines N2 of compressed B-mode images is wirelessly transmitted to the apparatus main body 2, and then the M-mode image compressed by the M-mode image compression processing unit 17B is wirelessly transmitted to the apparatus main body 2 at time T1 at which the wireless transmission of the B-mode images has been completed. The B-mode image and the M-mode image sequentially wirelessly transmitted in this manner are displayed on the monitor 33 of the apparatus main body 2.

As a result, the M-mode image is wirelessly transmitted later than the wireless transmission of the B-mode image, but each time the generation of the number of lines N2 of B-mode images, which is less than the number of scanning lines N1 in a single frame of the B-mode image, is performed, the B-mode image and the M-mode image are alternately wirelessly transmitted. Therefore, the delay time $\Delta T0$ of the M-mode image with respect to the B-mode image is reduced as compared with a conventional method of wirelessly transmitting the M-mode image after wirelessly transmitting the B-mode image on a frame-by-frame basis.

In addition, since the wireless transmission of the M-mode image is performed each time the generation of the number of lines N2 of B-mode images is performed, the M-mode image is wirelessly transmitted to the apparatus main body 2 at a short time interval D as compared with a conventional method of wirelessly transmitting the M-mode image after wirelessly transmitting a single frame of the B-mode image. Therefore, the M-mode image can be displayed on the monitor 33 of the apparatus main body 2 smoothly and at a stable frame rate. As a result, it is possible to perform intuitive diagnosis by observing the M-mode image displayed on the monitor 33 of the apparatus main body 2.

By repeating the wireless transmission of the B-mode images, which are compressed by the B-mode image compression processing unit 17A, for each number of lines N2 a plurality of times, a single frame of the B-mode image is generated and displayed on the monitor 33 of the apparatus main body 2, but the wireless transmission of the M-mode image is repeated a plurality of times while the single frame of the B-mode image is generated. In this way, a first frame B1 of the B-mode image is generated and displayed during the period of time T0 to time T2, similarly, a second frame B2 of the B-mode image is generated and displayed during the period of time T2 to time T3, a third frame B3 of the B-mode image is generated and displayed during the period of time T3 to time T4, and the M-mode images are wirelessly transmitted to the apparatus main body 2 at the time intervals D and smoothly displayed on the monitor 33 of the apparatus main body 2.

In a case where the communication environment between the ultrasound probe 1 and the apparatus main body 2 deteriorates and the wireless transmission rate in the wireless communication circuit 19 of the ultrasound probe 1 decreases, it may take time to transmit the B-mode images, which are compressed for each unit number of compression lines by the B-mode image compression processing unit 17A. Therefore, there is a risk that the wireless transmission of newly compressed B-mode images to the apparatus main body 2 may be attempted before the wireless transmission of previously compressed B-mode images is completed.

In that case, in a case where the wireless transmission rate in the wireless communication circuit 19 falls to or below a predetermined rate threshold value, the probe control unit 21 can control the wireless communication circuit 19 to discard the B-mode images in which the wireless transmission has not been completed through the wireless communication circuit 19 and to preferentially perform the wireless transmission of the M-mode image compressed by the M-mode image compression processing unit 17B to the apparatus main body 2.

For example, as shown in FIG. 9, in a case where the wireless transmission rate in the wireless communication circuit 19 falls to or below a predetermined rate threshold value, after time T2A, there may be a delay in the transmission of newly compressed B-mode images. In such a case, the B-mode images compressed by the B-mode image compression processing unit 17A and relating to the corresponding second frame B2 are discarded through the wireless communication circuit 19, and the wireless transmission of the M-mode image is preferentially performed. As a result, even after time T2A, the wireless transmission of the M-mode image at the time interval D is maintained, and the M-mode image can be smoothly displayed on the monitor 33 of the apparatus main body 2.

The B-mode image is wirelessly transmitted to the apparatus main body 2 again from a time in point when the communication environment is restored and the wireless transmission rate in the wireless communication circuit 19 exceeds the predetermined rate threshold value. FIG. 9 shows a state in which the B-mode images relating to the third frame B3 are wirelessly transmitted and displayed on the monitor 33 of the apparatus main body 2 from time T3. While the B-mode image is being discarded through the wireless communication circuit 19, the first frame B1 of the B-mode images that have been previously displayed on the monitor 33 of the apparatus main body 2 remains displayed as it is.

In addition, the M-mode images generated by the M-mode processing unit 15B are stored in the M-mode memory 16B and then are compressed for each unit number of compression lines set by the M-mode image compression processing unit 17B and wirelessly transmitted to the apparatus main body 2. By taking the difference between the M-mode images and performing reversible compression, the amount of data to be transmitted can be reduced.

In this way, in a case where a plurality of lines of M-mode images along the single scanning line SL are wirelessly transmitted together, the amount of time delay until transmission varies depending on the unit number of lines of the wireless transmission. In addition, the time required for wireless transmission varies depending on the communication environment.

In that case, the probe control unit 21 can control the wireless communication circuit 19 to make the unit number of lines for wireless transmission of the M-mode image variable according to the wireless transmission rate in the wireless communication circuit 19. By doing so, it is possible to maintain the wireless transmission of the M-mode image at a constant time interval D even in the presence of fluctuations in the communication environment, which makes it possible to smoothly display the M-mode image on the monitor 33 of the apparatus main body 2.

Further, in a case where the delay amount of the wireless transmission of the M-mode image by the wireless communication circuit 19 exceeds a predetermined delay threshold value due to fluctuations in the communication environment or the like, the probe control unit 21 may control the wireless communication circuit 19 to discard an untransmitted M-mode image. In this case, a loss occurs in the M-mode image, but in the apparatus main body 2, the M-mode image can be displayed on the monitor 33 with the loss portion blanked out. Similarly, in a case where a communication error occurs and results in a loss in the M-mode image, the M-mode image can be displayed on the monitor 33 with the loss portion blanked out.

In the above-described embodiment, as the apparatus main body 2, a portable or handheld compact apparatus main body can be used, and a stationary apparatus main body can also be used.

EXPLANATION OF REFERENCES

1: ultrasound probe
2: apparatus main body
11: transducer array
12: transmission circuit
13: reception circuit
14: transmission and reception control unit
B-mode processing unit
M-mode processing unit
16A: B-mode memory
16B: M-mode memory
17A: B-mode image compression processing unit
17B: M-mode image compression processing unit
18: multiplexer
19: wireless communication circuit
20: communication control unit
21: probe control unit
22: probe side processor
23: battery
31: wireless communication circuit 32: display control unit
33: monitor
34: communication control unit
35: main body control unit
36: input device
37: main body side processor
38: battery
41: amplification section
42: AD conversion section
43: beam former
44A, 44B: signal processing section
45A: DSC
46A, 46B: image processing section
ΔT0: delay time
UB: B-mode image
UM: M-mode image
SL: scanning line
ΔT, D: time interval
B1, B2, B3: frame

What is claimed is:

1. An ultrasound diagnostic apparatus comprising:
an ultrasound probe including a transducer array; and
an apparatus main body wirelessly connected to the ultrasound probe and including a monitor,
wherein the ultrasound probe includes
a probe-side processor configured to generate a B-mode image and an M-mode image, respectively, based on reception signals acquired by performing ultrasound scanning using the transducer array, and
a wireless communication circuit configured to wirelessly transmit the B-mode image and the M-mode image to the apparatus main body,
the probe-side processor controls the wireless communication circuit such that, each time a generation of a certain number of scanning lines in the B-mode image, which is less than the number of scanning lines in a single frame of the B-mode image, is completed, wireless transmission of the certain number of scanning lines in the B-mode image thus generated and wireless transmission of the M-mode image thus generated are alternately performed, and
the B-mode image and the M-mode image wirelessly transmitted from the ultrasound probe to the apparatus main body are displayed on the monitor.

2. The ultrasound diagnostic apparatus according to claim 1,
wherein the probe-side processor compresses each of the B-mode image and the M-mode image, and
the certain number of lines is a unit number of compression lines in compression of the B-mode image.

3. The ultrasound diagnostic apparatus according to claim 1,
wherein the probe-side processor monitors wireless transmission rate in the wireless communication circuit, and
the probe-side processor is configured to control the wireless communication circuit to transmit the M-mode image and to not transmit B-mode image in a case where a wireless transmission rate in the wireless communication circuit is at or below a predetermined rate threshold value.

4. The ultrasound diagnostic apparatus according to claim 2,
wherein the probe-side processor monitors wireless transmission rate in the wireless communication circuit, and
the probe-side processor is configured to control the wireless communication circuit to transmit the M-mode image and to not transmit B-mode image in a case where a wireless transmission rate in the wireless communication circuit is at or below a predetermined rate threshold value.

5. The ultrasound diagnostic apparatus according to claim 1,
wherein the probe-side processor monitors wireless transmission rate in the wireless communication circuit, and
the wireless communication circuit is configured to make a unit number of lines for the wireless transmission of the M-mode image variable according to a wireless transmission rate.

6. The ultrasound diagnostic apparatus according to claim 2,
wherein the probe-side processor monitors wireless transmission rate in the wireless communication circuit, and
the wireless communication circuit is configured to make a unit number of lines for the wireless transmission of the M-mode image variable according to a wireless transmission rate.

7. The ultrasound diagnostic apparatus according to claim 3,
wherein the wireless communication circuit is configured to make a unit number of lines for the wireless transmission of the M-mode image variable according to a wireless transmission rate.

8. The ultrasound diagnostic apparatus according to claim 4,
wherein the wireless communication circuit is configured to make a unit number of lines for the wireless transmission of the M-mode image variable according to a wireless transmission rate.

9. The ultrasound diagnostic apparatus according to claim 1,
wherein the probe-side processor is configured to control the wireless communication circuit to discard an untransmitted M-mode image in a case where a delay amount of the wireless transmission of the M-mode image by the wireless communication circuit exceeds a predetermined delay threshold value.

10. The ultrasound diagnostic apparatus according to claim 2,
wherein the probe-side processor is configured to control the wireless communication circuit to discard an untransmitted M-mode image in a case where a delay amount of the wireless transmission of the M-mode image by the wireless communication circuit exceeds a predetermined delay threshold value.

11. The ultrasound diagnostic apparatus according to claim 3,
wherein the probe-side processor is configured to control the wireless communication circuit to discard an untransmitted M-mode image in a case where a delay amount of the wireless transmission of the M-mode image by the wireless communication circuit exceeds a predetermined delay threshold value.

12. The ultrasound diagnostic apparatus according to claim 4,
wherein the probe-side processor is configured to control the wireless communication circuit to discard an untransmitted M-mode image in a case where a delay amount of the wireless transmission of the M-mode image by the wireless communication circuit exceeds a predetermined delay threshold value.

13. The ultrasound diagnostic apparatus according to claim 5,
wherein the probe-side processor is configured to control the wireless communication circuit to discard an untransmitted M-mode image in a case where a delay amount of the wireless transmission of the M-mode image by the wireless communication circuit exceeds a predetermined delay threshold value.

14. The ultrasound diagnostic apparatus according to claim 1,
wherein the apparatus main body includes a main body-side processor, and
the main body-side processor is configured to, in a case where there is a defect in the M-mode image wirelessly transmitted from the ultrasound probe, display the M-mode image on the monitor with the defect blanked out.

15. A control method for an ultrasound diagnostic apparatus in which an apparatus main body is wirelessly connected to an ultrasound probe including a transducer array, the control method comprising:
generating a B-mode image and an M-mode image through the ultrasound probe based on reception signals acquired by performing ultrasound scanning using the transducer array;
alternately performing, each time a generation of a certain number of scanning lines in the B-mode image, which is less than the number of scanning lines in a single frame of the B-mode image, is completed, wireless transmission of the generated certain number of scanning lines in the B-mode image from the ultrasound probe to the apparatus main body and wireless transmission of the generated M-mode image from the ultrasound probe to the apparatus main body; and
displaying the B-mode image and the M-mode image wirelessly transmitted from the ultrasound probe to the apparatus main body on a monitor of the apparatus main body.

16. The control method for an ultrasound diagnostic apparatus according to claim 15,
wherein the B-mode image and the M-mode image are each compressed and then wirelessly transmitted to the apparatus main body, and
the certain number of lines is a unit number of compression lines for the B-mode image.

17. The control method for an ultrasound diagnostic apparatus according to claim 15, wherein
the method further comprises monitoring wireless transmission rate from the transducer array to the apparatus main body, and
in a case where a wireless transmission rate from the transducer array to the apparatus main body is at or below a predetermined rate threshold value, the M-mode image is transmitted, and B-mode image is not transmitted.

18. The control method for an ultrasound diagnostic apparatus according to claim 15, wherein
the method further comprises monitoring wireless transmission rate from the transducer array to the apparatus main body, and
a unit number of lines for the wireless transmission of the M-mode image is made variable according to a wireless transmission rate from the transducer array to the apparatus main body.

19. The control method for an ultrasound diagnostic apparatus according to claim 15,
wherein, in a case where a delay amount of the wireless transmission of the M-mode image exceeds a predetermined delay threshold value, an untransmitted M-mode image is discarded.

20. The control method for an ultrasound diagnostic apparatus according to claim 15,
wherein, in a case where there is a defect in the M-mode image wirelessly transmitted from the ultrasound probe, the M-mode image is displayed on the monitor with the defect blanked out.

* * * * *